United States Patent
Rey et al.

(10) Patent No.: US 9,014,800 B2
(45) Date of Patent: Apr. 21, 2015

(54) PASSIVE ELECTRIC FIELD FOCUS SYSTEM FOR IN VIVO AND IN VITRO APPLICATIONS

(75) Inventors: Jose I. Rey, Tampa, FL (US); Richard Gilbert, Tampa, FL (US); Mark J. Jaroszeski, Wesley Chapel, FL (US); Richard Heller, Temple Terrace, FL (US)

(73) Assignee: University of South Florida, Tampa, FL (US)

( * ) Notice: Subject to any disclaimer, the term of this patent is extended or adjusted under 35 U.S.C. 154(b) by 779 days.

(21) Appl. No.: 12/246,958

(22) Filed: Oct. 7, 2008

(65) Prior Publication Data

US 2009/0131994 A1 May 21, 2009

Related U.S. Application Data

(63) Continuation of application No. PCT/US2007/008662, filed on Apr. 9, 2007.

(60) Provisional application No. 60/744,424, filed on Apr. 7, 2006, provisional application No. 60/745,530, filed on Apr. 25, 2006.

(51) Int. Cl.
  *A61N 1/05* (2006.01)
  *C12M 1/42* (2006.01)

(52) U.S. Cl.
  CPC .................................... *C12M 35/02* (2013.01)

(58) Field of Classification Search
  USPC ............ 607/2, 116; 604/20; 435/173.6, 285.2
  See application file for complete search history.

(56) References Cited

U.S. PATENT DOCUMENTS

| | | | |
|---|---|---|---|
| 5,273,525 A * | 12/1993 | Hofmann | ........................ 604/21 |
| 5,702,359 A | 12/1997 | Hofmann et al. | |
| 5,810,762 A | 9/1998 | Hofmann | |
| 5,858,192 A * | 1/1999 | Becker et al. | ................. 204/547 |
| 5,873,849 A * | 2/1999 | Bernard | ........................ 604/20 |
| 6,014,584 A | 1/2000 | Hofmann et al. | |
| 6,051,422 A | 4/2000 | Kovacs et al. | |
| 6,103,084 A | 8/2000 | Uhen | |
| 6,132,683 A | 10/2000 | Sugihara et al. | |

(Continued)

FOREIGN PATENT DOCUMENTS

| EP | 01237620 B1 | 11/2004 |
|---|---|---|
| EP | 01140282 B1 | 2/2005 |

(Continued)

OTHER PUBLICATIONS

Fotuhi et al., "Influence of epicardial patches on defibrillation threshold with nonthoracotomy lead configurations," Circulation. 1995;92: 3082-3088.*

*Primary Examiner* — Niketa Patel
*Assistant Examiner* — Christopher A Flory
(74) *Attorney, Agent, or Firm* — Molly Sauter; Smith & Hopen, P.A.

(57) ABSTRACT

The present invention provides a system and method of directing, focusing, or concentrating electrical charges within a defined electric field so that these charges can be used to exert forces on cells and tissues in vivo and/or cell cultures in vitro. The present invention reduces and/or eliminates the damage at a target site that would normally be caused by an electrode that acts as a current source or sink to accomplish the same task.

16 Claims, 12 Drawing Sheets
(12 of 12 Drawing Sheet(s) Filed in Color)

(56) References Cited

U.S. PATENT DOCUMENTS

| | | | |
|---|---|---|---|
| 6,135,990 A | 10/2000 | Heller et al. | |
| 6,181,964 B1 | 1/2001 | Hofmann et al. | |
| 6,278,895 B1 | 8/2001 | Bernard | |
| 6,393,325 B1* | 5/2002 | Mann et al. | 607/46 |
| 6,593,130 B1* | 7/2003 | Sen et al. | 435/285.2 |
| 6,977,172 B2 | 12/2005 | Burke et al. | |
| 6,988,006 B2* | 1/2006 | King et al. | 607/70 |
| 2002/0055703 A1 | 5/2002 | Mori et al. | |
| 2003/0104588 A1* | 6/2003 | Orwar et al. | 435/173.6 |
| 2003/0129716 A1 | 7/2003 | Ragsdale et al. | |
| 2004/0115784 A1* | 6/2004 | Dzekunov | 435/173.6 |
| 2005/0048651 A1* | 3/2005 | Ryttsen et al. | 435/459 |
| 2005/0054969 A1 | 3/2005 | Hoff et al. | |
| 2005/0192542 A1 | 9/2005 | Dev et al. | |
| 2005/0282284 A1 | 12/2005 | Rubinsky et al. | |
| 2006/0057706 A1 | 3/2006 | Miklavcic et al. | |
| 2006/0106441 A1* | 5/2006 | Ayal et al. | 607/118 |
| 2007/0287950 A1* | 12/2007 | Kjeken et al. | 604/21 |
| 2008/0045880 A1* | 2/2008 | Kjeken et al. | 604/21 |

FOREIGN PATENT DOCUMENTS

| | | |
|---|---|---|
| EP | 00866123 B1 | 3/2005 |
| EP | 01140283 B1 | 3/2006 |
| WO | 2005044371 A1 | 5/2005 |

* cited by examiner

PASSIVE ELECTRIC FIELD FOCUS SYSTEM FOR IN VIVO AND IN VITRO APPLICATIONS

CROSS REFERENCE TO RELATED APPLICATIONS

This application is a continuation of prior filed International Application, Ser. No. PCT/US2007/008662 filed Apr. 9, 2007, which claims priority to U.S. provisional patent application No. 60/744,424 filed Apr. 7, 2006 and U.S. provisional patent application No. 60/745,530 filed Apr. 25, 2006 which is hereby incorporated by reference into this disclosure.

GOVERNMENT SUPPORT

This invention was made with government support under Grant No. DGE-0221681 awarded by the National Science Foundation. The government has certain rights in the invention.

BACKGROUND OF THE INVENTION

Electroporation is known in the art as a method of treating a tissue in order to transiently increase the tissue's permeability to enhance molecular transport either for drug delivery or for sampling of interstitial fluids. Electroporation, or electropermeabilization, ellicits a significant increase in the electrical conductivity and permeability of the cell plasma membrane caused by an externally applied electrical field. Electroporation and electropermeabilization are known in the art. Some chemotherapeutic drugs used in cancer therapy have poor access into the tumor cells. Therefore, electropermeabilization offers an approach for increased drug delivery into the cells and thus better antitumor effectiveness. Tissues can also be electropermeabilized and thus the antitumor effectiveness of chemotherapeutic drugs potentiated by increasing drug delivery into the cells. It is known that electroporation can be performed both in vivo and in vitro.

Forces resulting from applied electric fields can be used on biological entities such as cells and tissues for many purposes that include cell breakdown, electrophoretic extraction or insertion of molecules, including electroporation or electropermeability, in addition to other forms of molecular manipulation know in the art.

In a system to apply electric fields to biological entities, a set of electrodes are used to establish an electric field within a biological entity. Currently, there is no system to direct, or focus, the established electric field intensity in in vivo and in vitro situations to a specific location within an electric field defined by the set of electrodes.

SUMMARY OF INVENTION

The present invention consists of a system and method of focusing electric fields for the purpose of exerting electrical forces on biological entities.

In accordance with the present invention, a system and method are provided for focusing an electric field intensity within a defined electric field to exert electrical forces on a biological entity. In a particular embodiment, the system includes, at least two active electrodes to establish an electric field within the biological entity and at least one passive electrode positioned within the path of the electric field to focus the electric field intensity of the established electric field at a desired location within the biological entity.

The system further includes a power source coupled to the at least two active electrodes to establish the electric field and software to control the field attributes, such as duration and intensity level. In this configuration, one of the electrodes is considered the source electrode and another of the electrodes is the sink electrode.

The system of the present invention is operation in both an in vivo and in vitro environment. In the case of an in vivo application, the biological entity may be a cell or group of cells, or a cellular tissue. In the case of an in vitro application, the biological entity may be a cell culture.

Various embodiments of the passive electrode are within the scope of the present invention. These embodiments include, but are not limited to, a passive electrode that is fabricated of a material from the group includes metals, semiconductors, nanoparticles, plastics, polymers, bio-polymers, fluidistic substances, bio-molecules, antibodies, proteins, DNA, RNA, non-conductive materials and high relative permittivity materials.

Additionally, the geometric configuration of the passive electrode may take on various forms. These forms include, but are not limited to, a star geometry, a four-corners geometry, a group of conductive needles, or a sphere for positioning below a surface level of the biological entity. The system of claim 1, wherein the passive electrode is shaped in a star geometry.

As such, the method of the present invention accomplishes the task of focusing the electric field within the biological entity by using a passive electrode(s) that does not act as a current source or sink for the field as defined by the set of electrodes used to generate the electric field. Accordingly, the present invention provides several advantages over existing technologies. The present invention provides a means of directing electric fields for application to living cells and tissues, facilitates in vivo electroporation in tissues that are in locations that are difficult to access, provides new applications and protocols for existing proprietary electroporation and/or electrofusion technologies, reduces and/or eliminates direct harm to cells and tissues at desired treatment sites caused by direct contact with active electrodes, and greatly improves the directional focus of the electric field.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which.

DETAILED DESCRIPTION OF THE PREFERRED EMBODIMENT

The method in accordance with the present invention takes advantage of a set of electric phenomena that occurs with changes in materials through an electric field's path. The electric field is redirected or concentrated in different places depending on the materials and different design geometries. How the method uses materials that vary in geometries and electrical characteristics such as conductivity and permittivity and different arrangements and geometries can be better explained by simple abstractions such as those in FIG. 1, where the electric field running between two electrodes is concentrated in the perpendicular direction of the applied electric field when using highly conducting materials, and in FIG. 2, where the electric field is concentrated in the direction of the applied electric field when using materials with relatively high permittivity.

Figure 1:
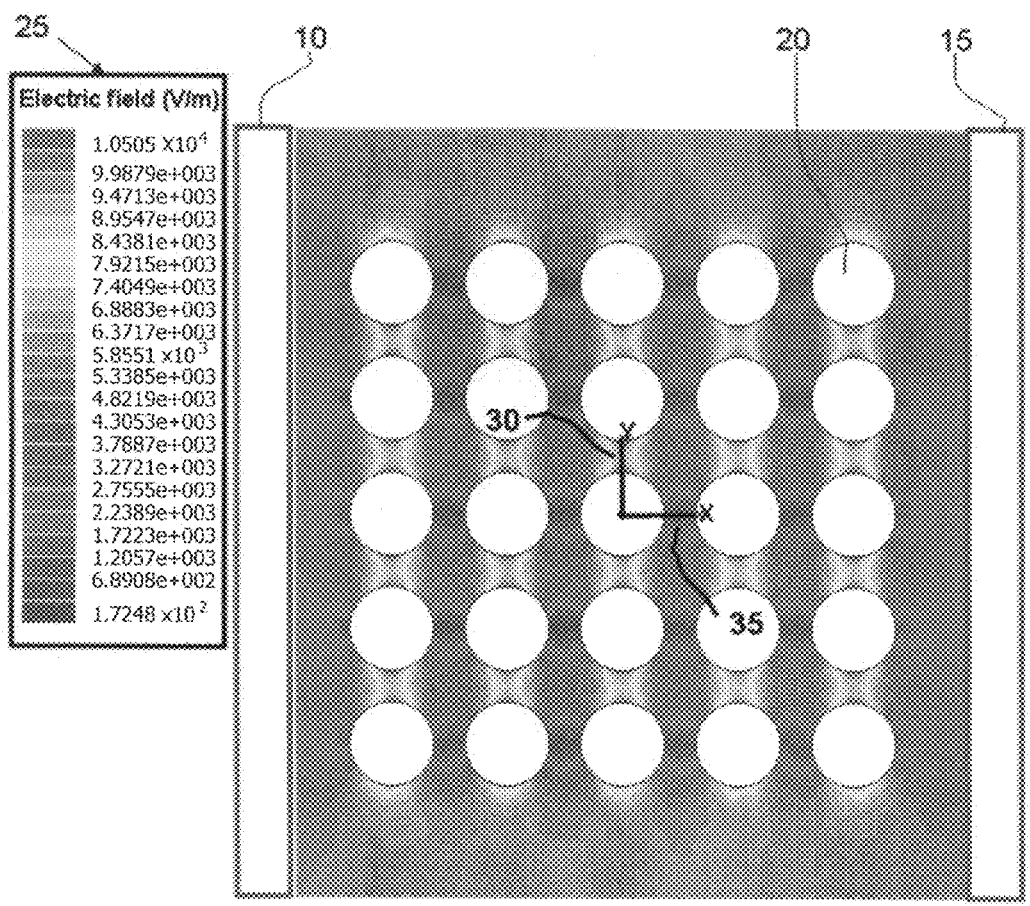
FIG. 1 is an illustrative example of an embodiment of the present invention wherein the electric field running between two electrodes is concentrated in the perpendicular direction of the applied electric field when using highly conductive materials.

With specific reference to FIG. 1, a 2D simulation illustrates an electric field running from the left electrode 10 to the right electrode 15. In this exemplary embodiment, the circles 20 in between the electrodes are made of platinum with the background being a vacuum. Platinum is an exemplary material and other conductive materials are within the scope of the present invention. As illustrated with reference to the accompanying legend 25, the highest electric field is shown as red shading and the lowest electric field is shown as blue shading. As such, the highly conductive circles 20 are effective in concentrating the electric field in the vertical direction (y) 30 when the applied electric field is running in the horizontal direction (x) 35.

Figure 2:
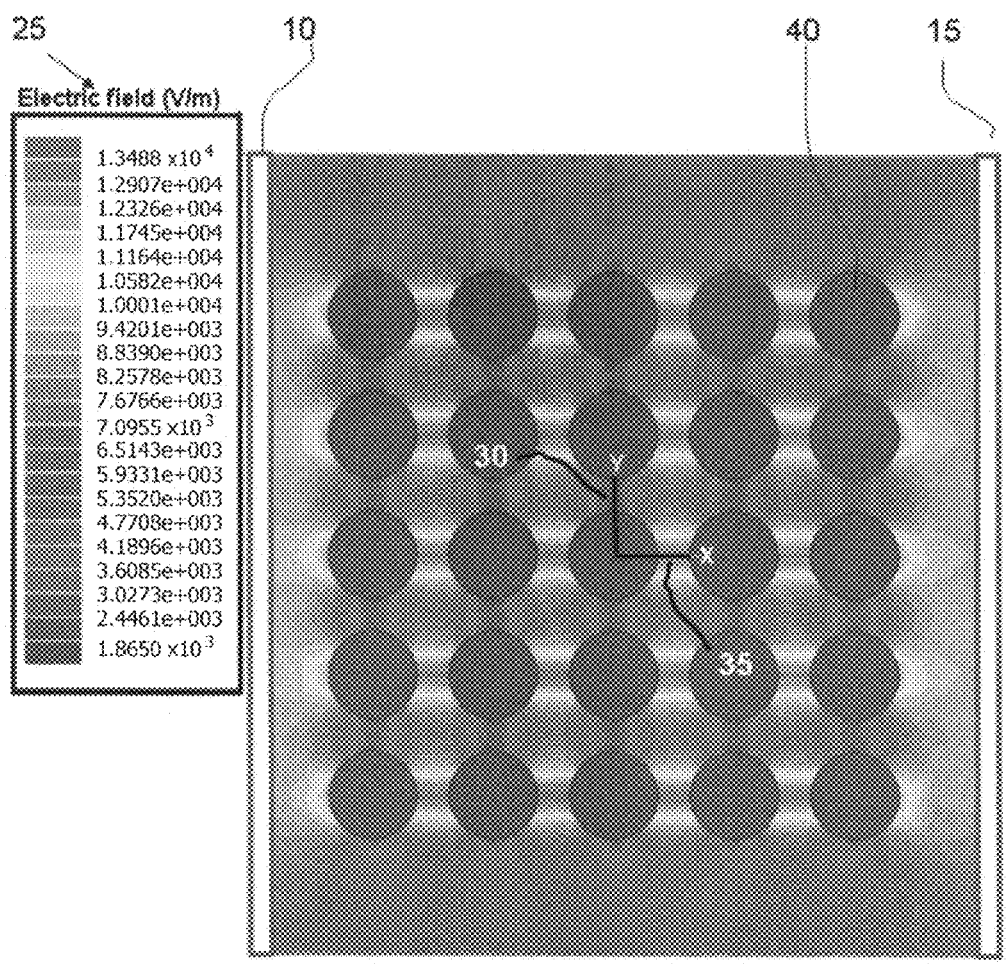
FIG. 2 is an illustrative example of an embodiment of the present invention wherein electric fields are concentrated in the direction of the applied electric field when using materials with relatively high permittivity.

With specific reference to FIG. 2, a 2D simulation illustrates an electric field running from the left electrode 10 to the right electrode 15. In this exemplary embodiment, the circles 20 in between the electrodes are made of mica with the background being a vacuum. Mica is an exemplary material and other materials having a substantially high permittivity are within the scope of the present invention. As illustrated with reference to the accompanying legend 25, the highest electric field is shown as red shading and the lowest electric field is shown as blue shading. As such, the high relative permittivity of the circles of mica 20 are effective in concentrating the electric field in the horizontal direction (x) 35 when the applied electric field is running in the same horizontal direction (x) 35.

The system in accordance with the present invention consists of a set of electrodes, having at least one current source electrode and at least one current sink electrode and a power source, a passive electrode and supporting software. The set of electrodes and associated power source are used to establish an electric field either in vivo or in vitro. The passive electrode is then placed in close proximity to the established electric field. The passive electrode is used to direct, concentrate, and/or focus charge at the location of the passive electrode and away from the current source and sink electrodes that define the shape of the overall electric field. This focused charge in an in vivo and/or in vitro application dramatically reduces, if not eliminates, the adverse effects of Joule heating and redox reactions that would occur at the location of the passive electrode if a current source or sink electrode were used instead of the passive electrode.

In accordance with the present invention, a passive electrode refers to a device that does not contain a source of electrical energy.

Figure 3:
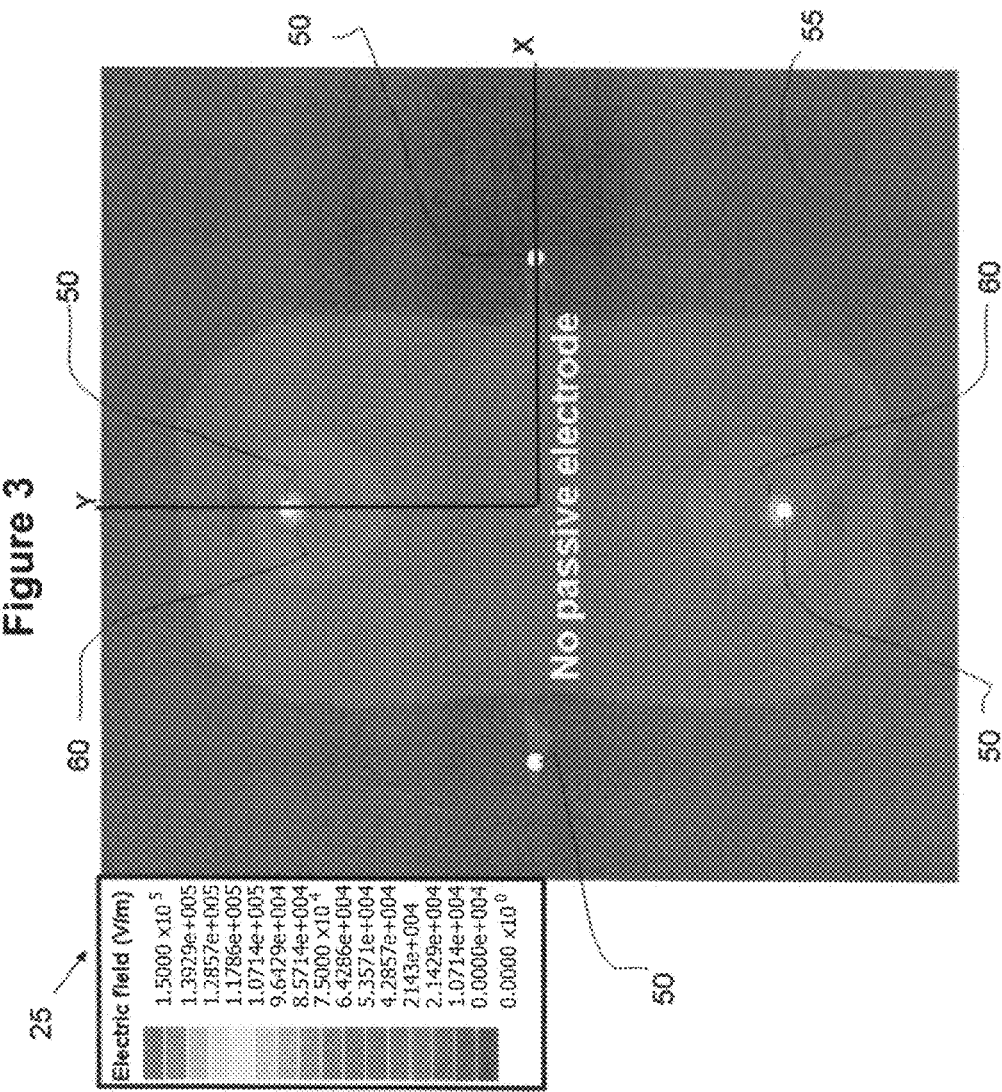
FIG. 3 illustrates the results corresponding to the magnitude of the electric field intensities resulting from the simulation wherein there is no passive electrode.
Figure 4:
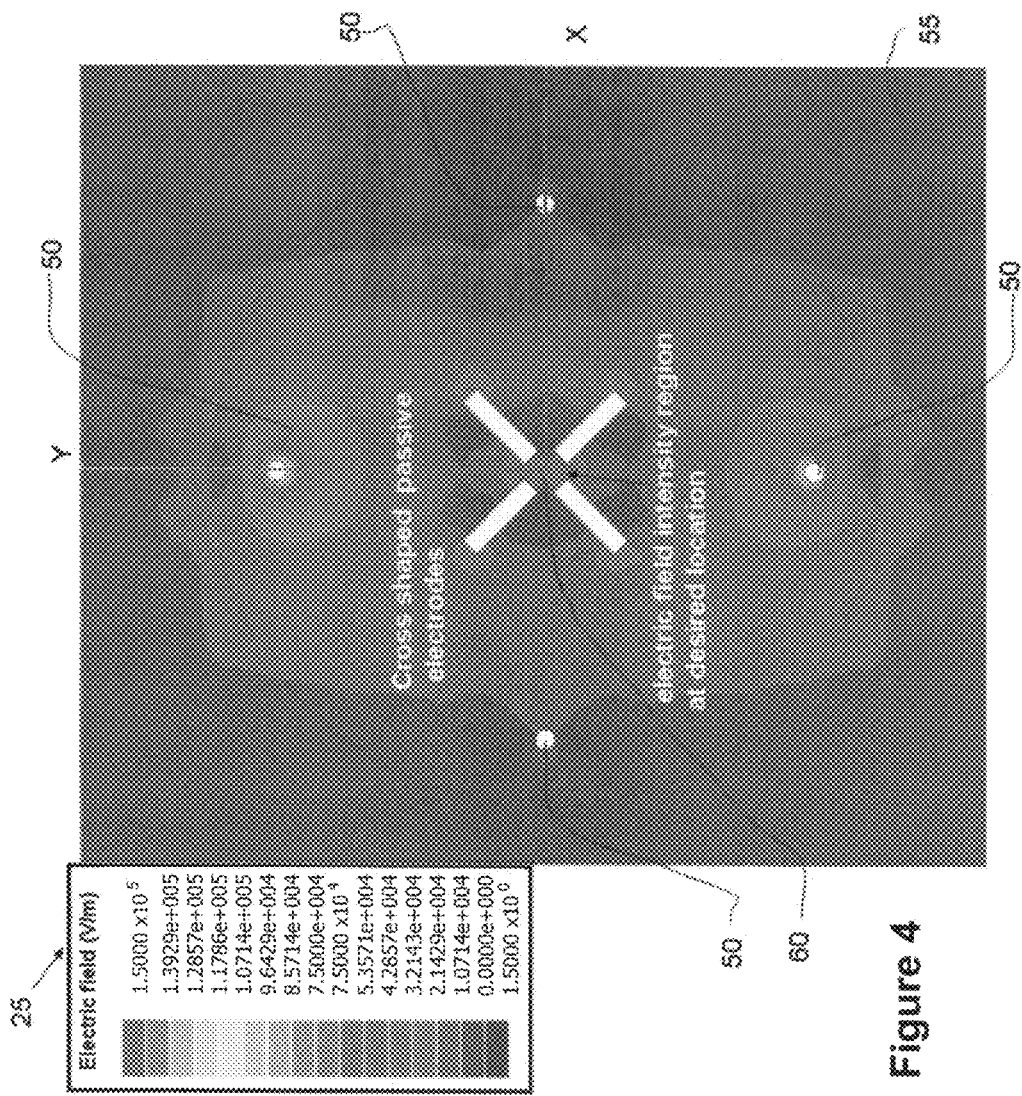
FIG. 4 illustrates an embodiment of the present invention showing the results corresponding to the magnitude of the electric field intensities resulting from a simulation wherein there is a passive electrode with a "star" geometry is positioned within the field.
Figure 5:
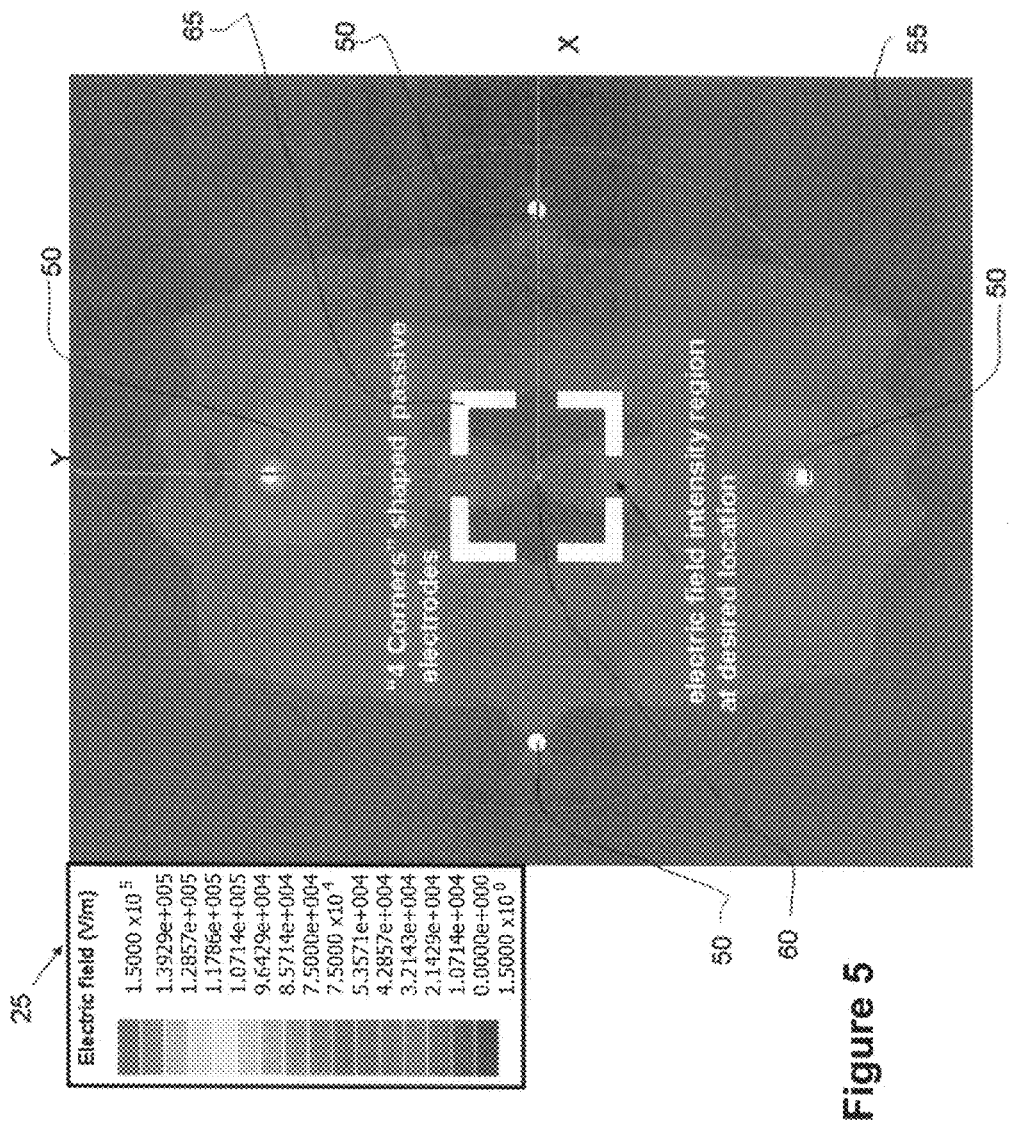
FIG. 5 illustrates an embodiment of the present invention showing the results corresponding to the magnitude of the electric field intensities resulting from a simulation wherein there is a passive electrode with a "four corners" applicator geometry.

With reference to FIG. 3, FIG. 4 and FIG. 5, an electrostatic simulation is illustrated as proof of concept of the invention. In this embodiment, a 5 cm plastic well with PBS solution is provided and four active electrodes 50 are used to apply current to the solution.

In FIG. 3, a passive electrode is not provided and the corresponding magnitudes of the electric field intensities that result from the simulation are illustrated, along with the legend 25 identify the associated colors. As shown, the lowest field intensity value is drawn in dark blue 55 (starting at 0V/m), and the most intense is drawn in red 60 (ending at 1.5V/m). It is expected that the areas where the electric field intensity is highest are the areas where charge will be focused and electroporation/electrofusion will be facilitated.

In FIG. 4, a passive electrode 65 with a "star" geometry is used and the corresponding magnitudes of the electric field intensities that result from the simulation are illustrated, along with the legend 25 identify the associated colors. As shown, the lowest field intensity value is drawn in dark blue 55 (starting at 0V/m), and the most intense is drawn in red 60 (ending at 1.5V/m). It is expected that the areas where the electric field intensity is highest are the areas where charge will be focused and electroporation/electrofusion will be facilitated.

In FIG. 5, a passive electrode 70 with a "four corners" geometry is used and the corresponding magnitudes of the electric field intensities that result from the simulation are illustrated, along with the legend 25 identify the associated colors. As shown, the lowest field intensity value is drawn in dark blue 55 (starting at 0V/m), and the most intense is drawn in red 60 (ending at 1.5V/m). It is expected that the areas where the electric field intensity is highest are the areas where charge will be focused and electroporation/electrofusion will be facilitated.

The simulation results illustrated in FIG. 3-FIG. 6, are shown in a 2 dimensional space, but applications and design of applications are accomplished in a 3 dimensional space. The geometries presented here serve to indicate concept feasibility. Actual applicator design will be adjusted to the reality of cell and/or tissue 3D space.

Figure 6:
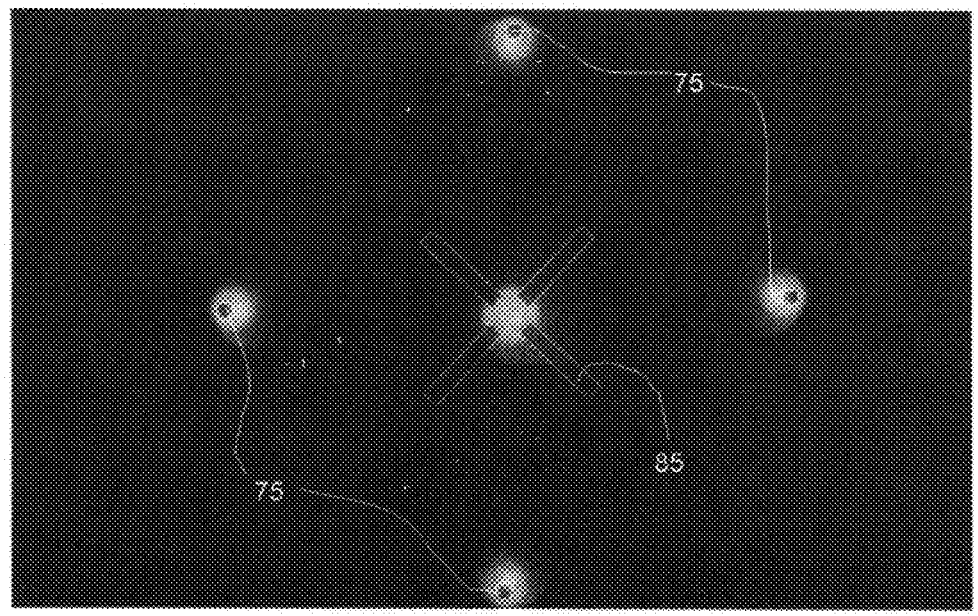
FIG. 6 illustrates actual results for a prototype "star" geometry applicator in accordance with the present invention.

FIG. 6 illustrates how the concept of the present invention is proven by generating electroporation in the zone where the electric fields should be higher according to the simulation in FIG. 4, as previously described. FIG. 6 illustrates actual results for a prototype "star" geometry passive electrode as described in the simulations presented above. The "greenish" color is the result of electroporation and subsequent florescence of an electroporation sensitive biomarker. The four peripheral green circular areas in the figure indicate the electroporation that has occurred at each of the four current source/current sink active electrodes. The color region in the middle of the figure reflects electroporation at the passive "star" configured electrode. The absence of color in the remaining area of the figure illustrates that electroporation is limited to the targeted electroporation site at the location of the passive electrode.

The materials that compose the active electrodes and/or the passive electrodes include but are not limited to the following: (1) Metals, (2) Semiconductors, (3) Nanoparticles, (4) Non-metals such as plastic, Polymers, Bio-polymers, (5) Fluidistic substances, (6) Bio-molecules such as antibodies, proteins, DNA, and RNA, (7) Non-conductive materials and (8) High relative permittivity materials.

Additionally, the passive electrode can be anything that is in the path of the electric field, and may be native to the biological system that is being treated and thus does not need to be introduced prior to the electric field being established. The passive electrode is positioned in the path of the electric fields between the sink and the source electrode(s). Passive electrodes can be inside or outside the biological entity, and are not limited to foreign entities, but in additional may be intrinsic to the entity. For example, the active electrodes may be positioned such that a bone within the biological entity becomes the passive electrode.

The passive electrode may take the form of a fluid which can change its shape, volume and conformation to change its field distribution characteristics. When the passive electrode is a fluid, the fluid will take on different concentration profiles and 3D shapes over time. It is also know that a fluid passive electrode can change its position or be induced to change its position relative to the active electrodes as necessary.

The passive electrode in accordance with the present invention may be inside or outside of the biological entity. In addition, it can remain permanently with the biological entity or be removed after it has served its purpose. Alternatively, the passive electrode may become an active electrode. For example, a passive electrode that experiences a chemical reaction that results in a potential difference, or a passive electrode that is grounded after it has served its purpose would result in a change from a passive electrode to an active electrode. Additionally, the electrical characteristics of the passive electrode may change so that the electric field is affected differently. For example, the passive electrode may be fabricated of a material that changes conductivity under temperature conditions.

When utilizing an in vivo application, the device and components could be located in any tissue of a living being not restricted to a single geographic localization.

Possible geometries are not limited to those in the proof of concept device; such geometry was only used to demonstrate the principle behind the application of electric fields by passive electroporation on living cells and biomolecules.

Figure 7A:
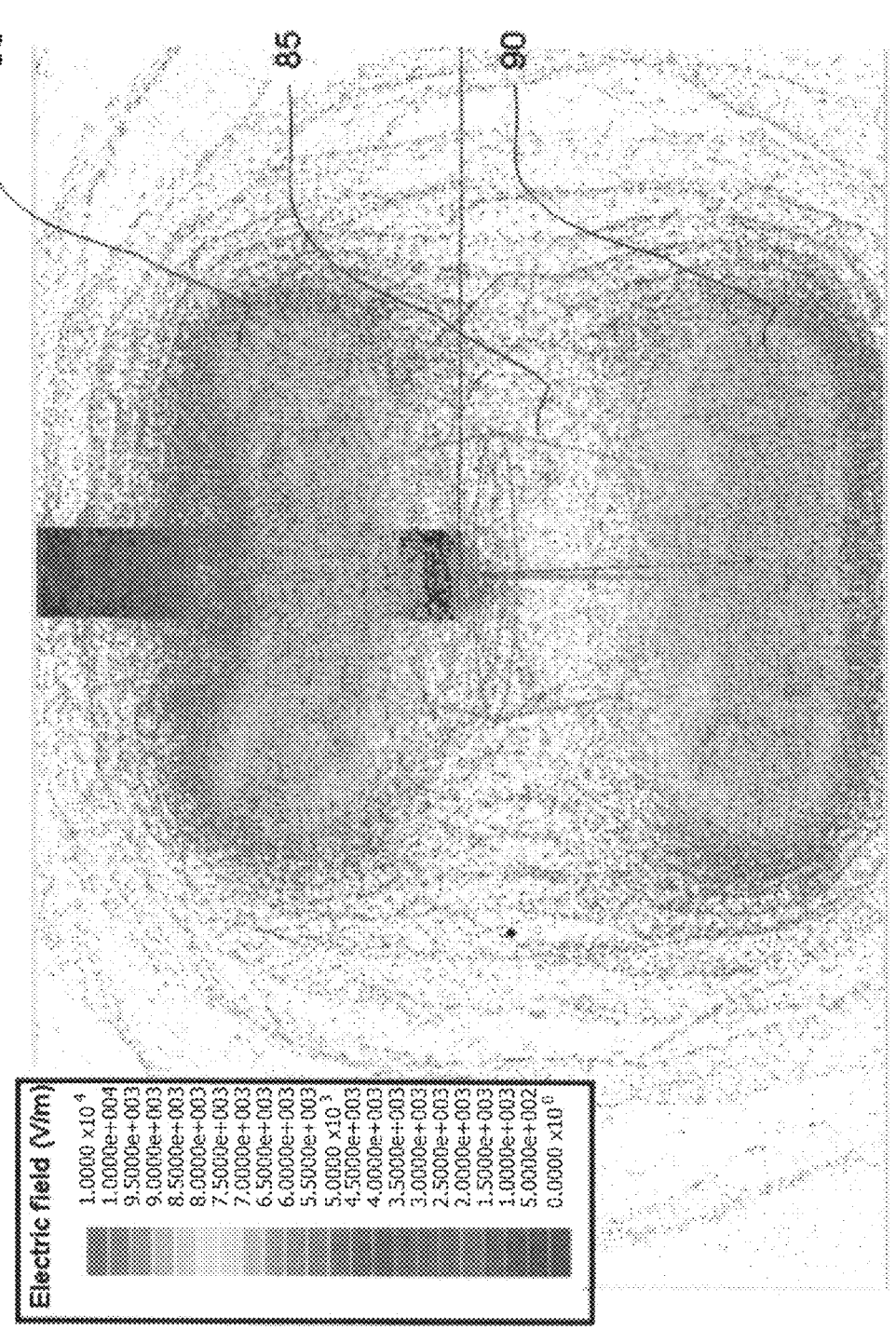
FIGS. 7A and 7B illustrate the results of improved electroporation at the site of an implantable device in accordance with the present invention.
Figure 7B:
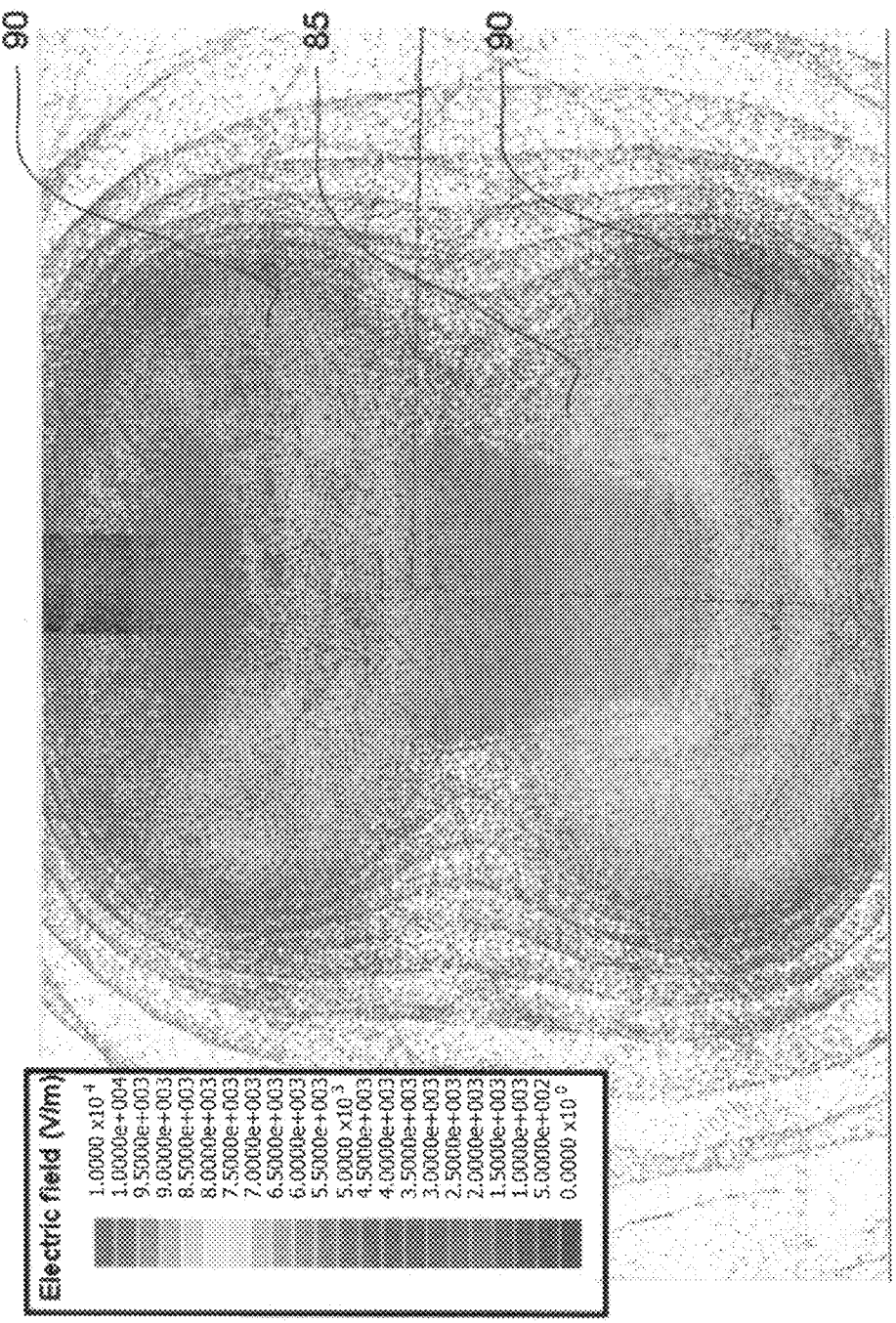

With reference to FIGS. 7A and 7B, in an exemplary embodiment it is shown that improved electroporation can be accomplished at the site of an implantable device. The concentration of electric fields can be induced at a specific site by using micro-metallic beans or composed material beads. In this embodiment an applied electric field is concentrated in living tissue near the site of an implantable device in vivo. In this embodiment, the electric fields are concentrated in the larger green volume 85 in between the two electrodes 90 in the images because of micro-beads of conductive material that are suspended in a hydrogen or other type of biocompatible matrix.

Figure 8A:
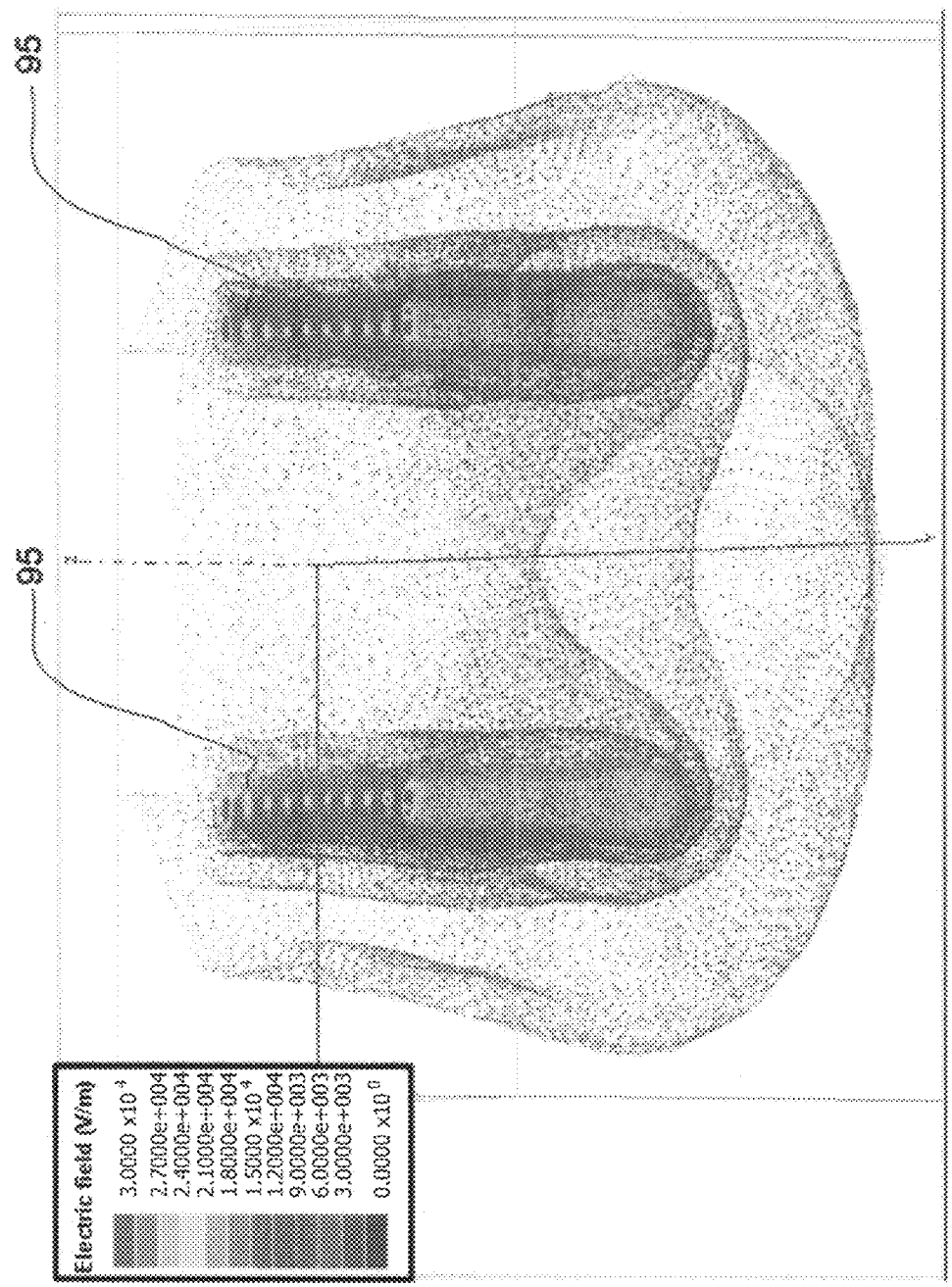
FIGS. 8A and 8B illustrate the results of improved electroporation for a needle electroporation application in accordance with the present invention.
Figure 8B:
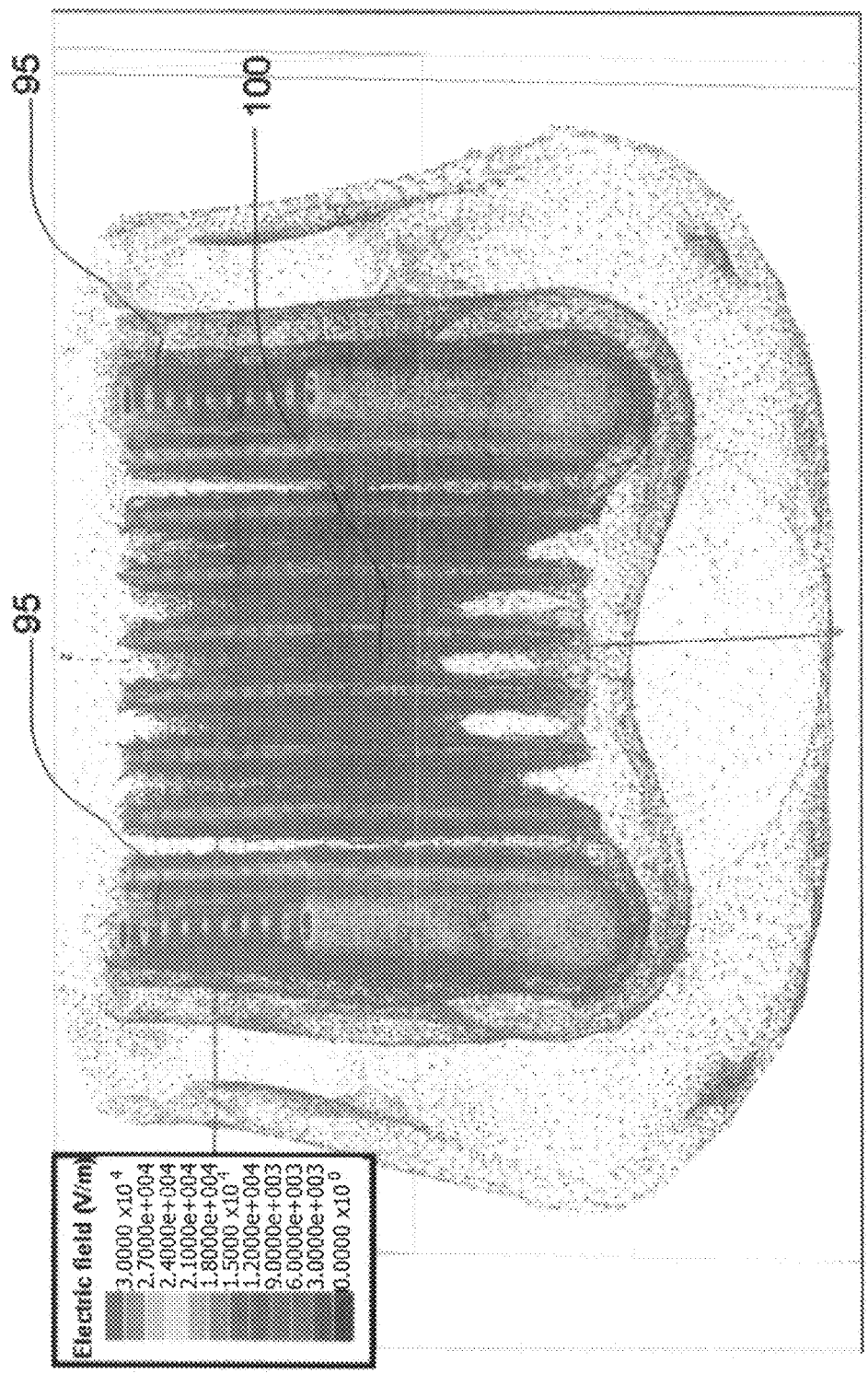

With reference to FIGS. 8A and 8B, in an exemplary embodiment it is shown that improved electroporation can be accomplished utilizing a plurality of needles as the passive application. By using a combination of materials as composing the needles, it is possible to direct currents in specific directions or depths. FIGS. 8A and 8B show an electric field as it is applied from electrodes 95 located at the left and right in the volume. In this embodiment, passive conductive needles 100 are added in between the active electrodes, with no other changes to geometries or variables, the charges are concentrated at the location of the passive needles. This configuration improves current state of the art in vivo electroporation devices.

Figure 9:
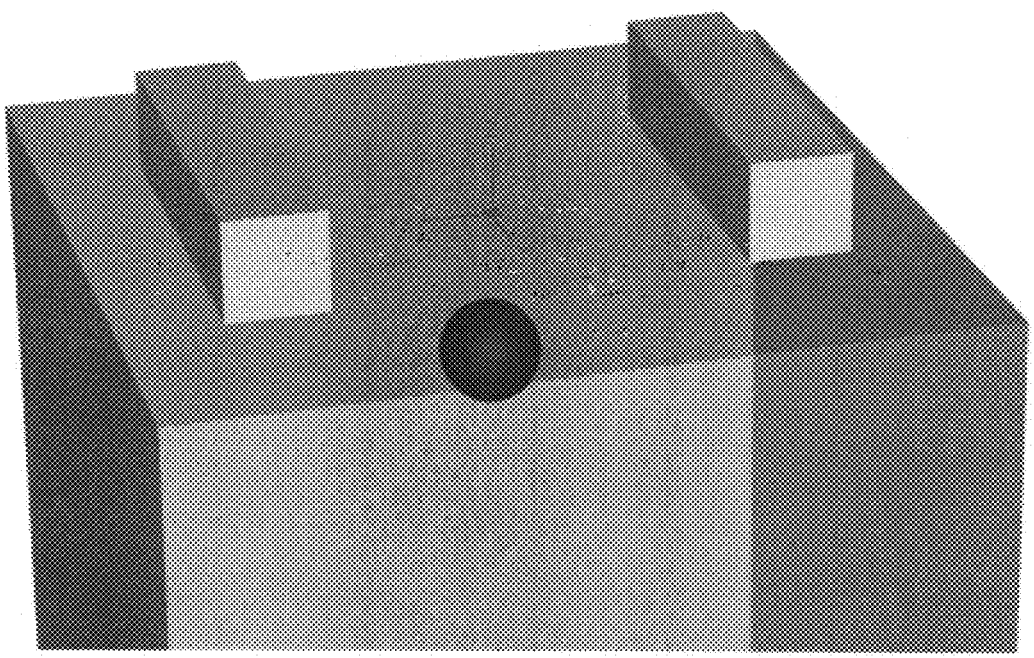
FIG. 9 illustrates a simulation of an implantable electroporation device that concentrates electric fields under living tissue employing a sphere.
Figure 10:
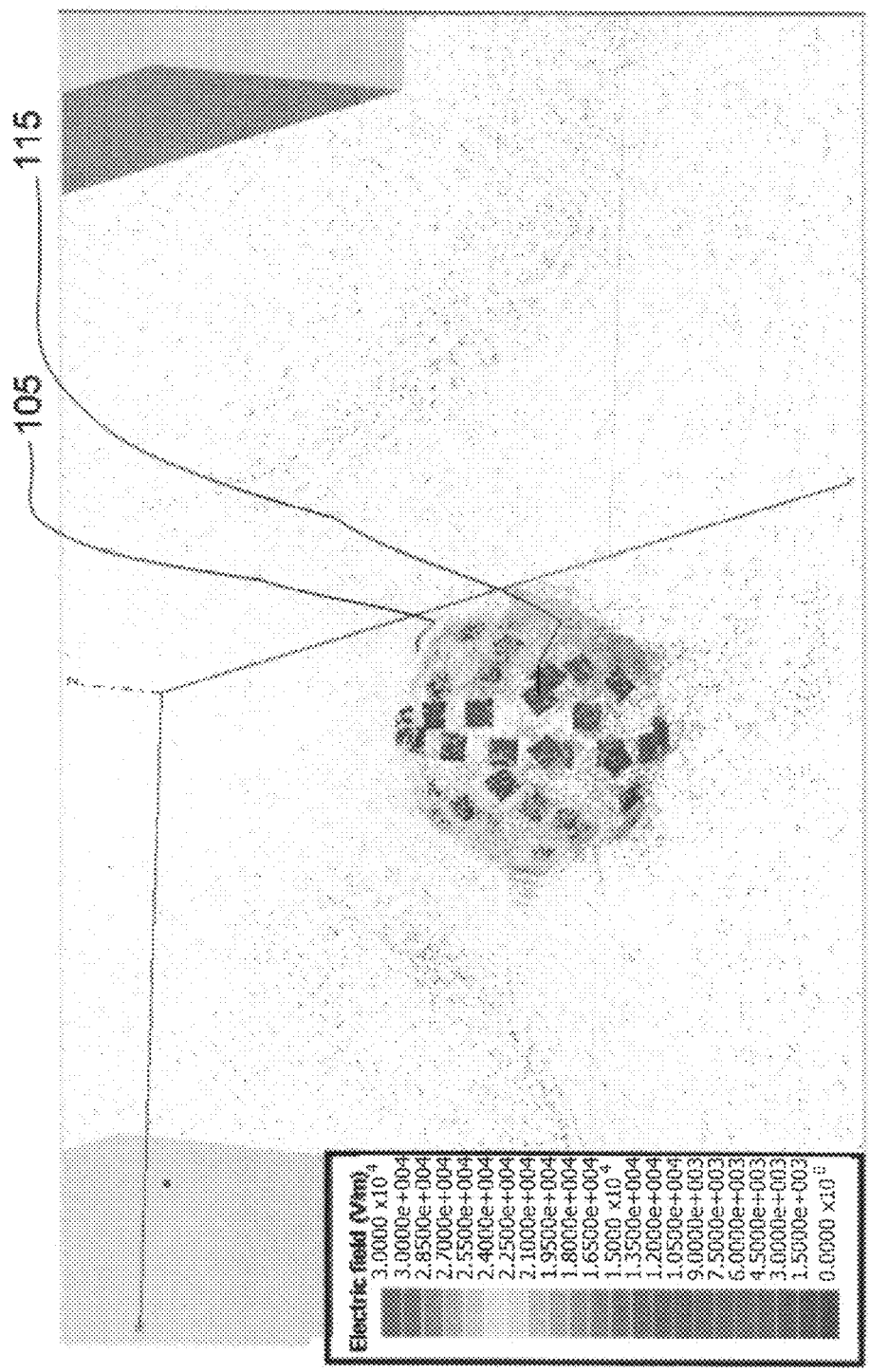
FIG. 10 illustrates a simulation of an implantable electroporation device that concentrates electric fields under living tissue employing a hollow sphere.

With reference to FIG. 9 and FIG. 10, in an exemplary embodiment it is shown that improved electroporation can be accomplished utilizing an implantable electroporation device. FIG. 9 and FIG. 10 show a simulation of an implantable electroporation device 105 that concentrates electric fields under living tissue. The first configuration, illustrated in FIG. 9, is an implanted sphere 105 that serves to concentrate charges established by the electrodes 110 under living tissue conditions. Additionally, as illustrated in FIG. 10, the sphere can be either hollow or filled with a different material, and the surface of the sphere 105 may have a set of shell particles 115 that help concentrate charges as shown by the higher electric fields (red dots around surface of sphere). Different configurations of this device can achieve many applications. Additionally the passive electrode may take the form of a container for any agent. For example, the passive electrode may be a hollow sphere containing a drug for delivery to the biological entity.

In an additional embodiment, the passive electrode may function as a scaffold for biological structures. For example, the passive electrode may function as a scaffold for bone growth when used in vivo.

In an additional embodiment, the passive electrode is labeled to allow the identification of the position of the passive electrode within the entity at any point in time. The passive electrode may be fluorescent labeled, radio-labeled, magnetically labeled or contrast agent labeled, in addition to other such labeling techniques known in the art.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of focusing an electric field within a defined electric field to facilitate electroporation within a biological entity, the method comprising the steps of:

establishing an electric field between at least one first active electrode and at least one second active electrode within the biological entity, the established electric field having an electric field intensity concentration focus; and changing the focus of the electric field intensity concentration to facilitate electroporation at a desired focus location within the biological entity by positioning a passive electrode within the electric field established between the at least one first active electrode and the at least one second active electrode, wherein the passive electrode is fabricated of a material selected from the group consisting of metals, semiconductors, nanoparticles, plastics, polymers, bio-polymers, fluidistic substances, bio-molecules, non-conductive materials and high relative permittivity materials, wherein the passive electrode is not a current source or a current sink for the established electric field, wherein the passive electrode is never physically or electrically coupled to a source of electrical energy and wherein the passive electrode is never physically or electrically coupled to another passive electrode or to a conducting element.

2. The method of claim 1, wherein the at least one first active electrode is a source electrode and the at least one second active electrode is a sink electrode.

3. The method of claim 1, wherein the establishment of the electric field is controlled by software means.

4. The method of claim 1, wherein the biological entity is in vivo.

5. The method of claim 1, wherein the biological entity is in vitro.

6. The method of claim 1, wherein the passive electrode is a fluid.

7. The method of claim 6, wherein a concentration profile of the fluid passive electrode changes over time.

8. The method of claim 6, wherein a shape of the fluid passive electrode changes over time.

9. The method of claim 1, wherein the passive electrode is internal to die biological entity.

10. The method of claim 1, wherein the passive electrode is removable.

11. The method of claim 1, wherein the passive electrode is a container fbr an agent.

12. The method of claim 11, wherein the agent is a drug for delivery into the biological entity.

13. The method of claim 1, wherein the passive electrode is a scaffold for biological structures within the biological entity.

14. The method of claim 1, wherein the passive electrode is labeled.

15. The method of claim 1, wherein the passive electrode further comprises a plurality of electrical characteristics and said electrical characteristics vary dependent upon varying environmental conditions.

16. The method of claim 15, wherein one of the plurality of electrical characteristics is conductivity, and said conductivity of the passive electrode changes under varying temperature conditions.

* * * * *

UNITED STATES PATENT AND TRADEMARK OFFICE
CERTIFICATE OF CORRECTION

| | | |
|---|---|---|
| PATENT NO. | : 9,014,800 B2 | Page 1 of 1 |
| APPLICATION NO. | : 12/246958 | |
| DATED | : April 21, 2015 | |
| INVENTOR(S) | : Jose I. Rey et al. | |

It is certified that error appears in the above-identified patent and that said Letters Patent is hereby corrected as shown below:

In the Claims

Column 8, Claim 9, Line 6 should read:

internal to the biological entity.

Column 8, Claim 11, Line 10 should read:

a container for an agent.

Signed and Sealed this
Eighth Day of September, 2015

Michelle K. Lee
*Director of the United States Patent and Trademark Office*